(12) United States Patent
Kawazoe

(10) Patent No.: US 7,262,316 B2
(45) Date of Patent: Aug. 28, 2007

(54) PROCESS FOR PRODUCING AROMATIC NITRILE COMPOUND

(75) Inventor: Kentaro Kawazoe, Shizuoka (JP)

(73) Assignee: Ihara Chemical Industry Co., Ltd. (JP)

( * ) Notice: Subject to any disclaimer, the term of this patent is extended or adjusted under 35 U.S.C. 154(b) by 10 days.

(21) Appl. No.: 10/531,171

(22) PCT Filed: Oct. 20, 2003

(86) PCT No.: PCT/JP03/13373

§ 371 (c)(1),
(2), (4) Date: Apr. 11, 2005

(87) PCT Pub. No.: WO2004/035526

PCT Pub. Date: Apr. 29, 2004

(65) Prior Publication Data

US 2006/0069282 A1 Mar. 30, 2006

(30) Foreign Application Priority Data

Oct. 21, 2002 (JP) .............................. 2002-305742
Jul. 18, 2003 (JP) .............................. 2003-276507

(51) Int. Cl.
C07C 253/00 (2006.01)
C07C 255/45 (2006.01)
C07C 255/49 (2006.01)

(52) U.S. Cl. ...................... 558/308; 558/309; 558/315; 558/316; 558/318; 558/329

(58) Field of Classification Search ................ 558/315, 558/308, 309, 316, 318, 329
See application file for complete search history.

(56) References Cited

U.S. PATENT DOCUMENTS 4,929,634 A * 5/1990 Herman et al. ............. 514/426
5,618,965 A * 4/1997 Kudschus .................. 558/315
6,433,195 B1 * 8/2002 Ikemoto et al. ............. 549/467
7,102,025 B2 * 9/2006 Kataoka et al. ............. 558/315

FOREIGN PATENT DOCUMENTS

JP 55-153759 11/1980
JP 56-2951 1/1981

* cited by examiner

*Primary Examiner*—Rebecca Anderson
*Assistant Examiner*—Jason M Nolan
(74) *Attorney, Agent, or Firm*—Bacon & Thomas, PLLC

(57) ABSTRACT

A novel process for industrially producing an aromatic nitrile compound represented by the following general formula (3):

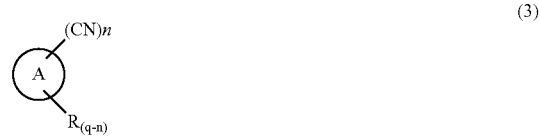

(3)

characterized in that one of an aromatic hydroxymethyl compound, an aromatic alkoxymethyl compound and an aromatic aldehyde compound, all represented by the following general formula (1):

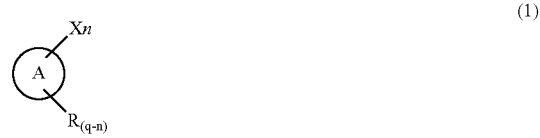

(1)

or a mixture thereof is reacted with an oxidized bromine compound represented by the general formula (2)

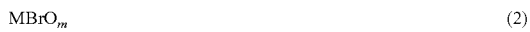

$MBrO_m$ (2)

in the presence of an acid catalyst and either ammonia or an ammonium sat.

8 Claims, No Drawings

PROCESS FOR PRODUCING AROMATIC NITRILE COMPOUND

CROSS-REFERENCE TO RELATED APPLICATIONS

This application is a National Phase Application (35 USC 371) of PCT/JP2003/013373 and claims priority of Japanese Application No. 2002-305742 filed Oct. 21, 2002 and Japanese Application No. 2003-276507 filed Jul. 18, 2003.

TECHNICAL FIELD

The present invention relates to a process for producing an aromatic nitrile compound by oxidizing one of an aromatic hydroxymethyl compound, an aromatic alkoxymethyl compound and an aromatic aldehyde compound, or a mixture thereof in the presence of ammonia or the like as a nitrogen source.

BACKGROUND ART

Various processes have been known heretofore for production of an aromatic nitrile compound from a raw material compound which is an aromatic hydroxymethyl compound, an aromatic alkoxymethyl compound or an aromatic aldehyde compound.

There are known, for example, processes which comprise reacting an aromatic hetero-cyclic aldehyde [e.g. furfural (2-furylaldehyde), 2-thienylaldehyde or 3-pyridylaldehyde] or an aromatic aldehyde (e.g. benzaldehyde) with a hydroxyamine salt to form an oxime and then dehydrating the oxime to produce a corresponding nitrile (e.g. furonitrile) [see Synthetic Communications, Vol. 30, pp. 3109-3114 (2000); Synthesis, pp. 190-191 (1982); Synthesis, pp. 243-246 (2003); Synthetic Communications, Vol. 13 No. 12, pp. 999-1006 (1983)].

These processes, however, comprise two steps of oxime formation and subsequent dehydration; require a dehydrating reagent (e.g. phtalic anhydride or methanesulfonyl chloride) of ordinarily at least one equivalent; when hydroxyamine sulfate is used, it is difficult in some cases to separate the formed aromatic nitrile compound from an inorganic sulfate.

There is also known a process which comprises reacting an aromatic aldehyde with ammonia gas in a gas phase in the presence of a catalyst consisting of copper and a solid acid, to produce an aromatic nitrile compound (JP-A-2000-239247). In this process, however, catalyst preparation need be conducted at a high temperature of 500° C. and excessive ammonia of 2.7 to 10.3 equivalents is required, which is disadvantageous industrially; moreover, a special facility is required for a gas phase reaction at high temperatures of 280 to 330° C.; furthermore, the raw material aldehyde compound is not usable when it is thermally unstable or has a high boiling point, which is a drawback.

There is also known a process for converting an aromatic aldehyde into a corresponding aromatic nitrile compound, using sodium azide in the presence of aluminum chloride [Synthesis, Vol. 7, pp. 641-642 (1992)]. However, use of highly toxic sodium azide in 6 equivalents and aluminum chloride in 2 equivalents is not preferred in industrial practice of the process, from the standpoint of safe operation.

There is further known a process using either of an aromatic aldehyde and benzyl alcohol, and aqueous ammonia and potassium peroxodisulfate in the presence of a nickel catalyst [Chemistry Letters, Vol. 4, pp. 571-574 (1990)]. In this process, however, there are problems that a large excess of ammonia (10 equivalents) is required and, moreover, a benzoic acid compound corresponding to the raw material used is formed as a by-product in an amount of 10 to 20%.

Thus, in the technical field to which the present invention belongs, it has been desired to solve the drawbacks of the prior art and develop a process which can produce an aromatic nitrile compound easily under mild conditions without using a special reaction apparatus or a special reaction reagent.

In view of such a situation, the present inventor made a study on a process which can produce an aromatic nitrile compound from either of an aromatic hydroxymethyl compound, an aromatic alkoxymethyl compound and an aromatic aldehyde compound, or from a mixture thereof. As a result, the present inventor found unexpectedly that the above aim could be solved by reacting the above aromatic compound with an oxidized bromine compound in the presence of an acid catalyst, using ammonia or the like as a nitrogen source. The present invention has been completed based on this finding.

DISCLOSURE OF THE INVENTION

The present invention has achieved the above aim by providing the inventions mentioned in the following [1] to [17].

[1] A process for producing an aromatic nitrile compound represented by the following general formula (3):

[wherein ring A is an aromatic hetero-cycle having at least one hetero-atom or a phenyl ring;

n is an integer of 1 to 9;

R is a hydrogen atom, an alkyl group, a hydroxyl group, an alkoxy group, a hydroxyalkyl group, an alkoxyalkyl group, a haloalkyl group, a carboxyl group or a metal salt thereof, an alkoxycarbonyl group, a halogen atom, a nitro group, an amino group, an alkylamino group, a dialkylamino group, an alkylcarbonylamino group, a cyano group, a formyl group, an alkylcarbonyl group, or a substituted or unsubstituted phenyl group; q is an integer of 1 to 9 with a proviso that (q–n) is zero or a positive integer; when (q–n) is 2 or more, a plurality of Rs may be the same or different; two Rs may be bonded to each other to form a ring], characterized in that one of an aromatic hydroxymethyl compound, an aromatic alkalkoxymethyl compound and an aromatic aldehyde compound, all represented by the following general formula (1):

(wherein X is a hydroxymethyl group, an alkoxymethyl group or a formyl group; n, R and q have the same definitions as given above), or a mixture thereof is reacted with an oxidized bromine compound represented by the general formula (2)

$$MBrO_m \quad (2)$$

(wherein M is a hydrogen atom or a metal atom, and m is an integer of 1 to 3) in the presence of an acid catalyst and either ammonia or an ammonium salt.

[2] A process for producing an aromatic nitrile compound according to [1], wherein the ring A is an aromatic heterocycle having at least one hetero-atom.

[3] A process for producing an aromatic nitrile compound according to [2], wherein the hetero-atom is selected from the group consisting of nitrogen atom, oxygen atom and sulfur atom.

[4] A process for producing an aromatic nitrile compound according to [2], wherein the ring A is a 5- to 10-membered aromatic hetero-ring having 1 to 3 hetero-atoms selected from the group consisting of nitrogen atom, oxygen atom and sulfur atom.

[5] A process for producing an aromatic nitrile compound according to [2], wherein the ring A is a furan ring, a thiophene ring, a pyridine ring, a quinoline ring or a thiazole ring.

[6] A process for producing an aromatic nitrile compound according to [1], wherein the ring A is a phenyl ring.

[7] A process for producing an aromatic nitrile compound according to [1], wherein the raw material compound represented by the general formula (1) is a compound of the general formula (1) wherein all of a plurality of Rs are hydrogen atom or at least one of a plurality of Rs is an electron-withdrawing group or an alkyl group.

[8] A process for producing an aromatic nitrile compound according to [7], wherein the compound represented by the general formula (1) is a compound of the general formula (1) wherein all of a plurality of Rs are hydrogen atom or at least one of a plurality of Rs is a chloro group, a nitro group, a fluoro group or a methyl group.

[9] A process for producing an aromatic nitrile compound according to [1], wherein the oxidized bromine compound represented by the general formula [2] is bromic acid, a bromate or a bromite.

[10] A process for producing an aromatic nitrile compound according to [9], wherein the oxidized bromine compound represented by the general formula (2) is a bromate.

[11] A process for producing an aromatic nitrile compound according to [1], wherein the acid catalyst is an organic carboxylic acid.

[12] A process for producing an aromatic nitrile compound according to [11], wherein the acid catalyst is acetic acid.

[13] A process for producing an aromatic nitrile compound according to [1], wherein the oxidized bromine compound represented by the general formula (2) is a bromate or a bromite and the acid catalyst is an organic carboxylic acid.

[14] A process for producing an aromatic nitrile compound according to [13], wherein the oxidized bromine compound represented by the general formula (2) is a bromate and the acid catalyst is an organic carboxylic acid.

[15] A process for producing an aromatic nitrile compound according to [14], wherein the oxidized bromine compound represented by the general formula (2) is a bromate or a bromite and the acid catalyst is acetic acid.

[16] A process for producing an aromatic nitrile compound according to [13], wherein the oxidized bromine compound represented by the general formula (2) is a bromate and the acid catalyst is acetic acid.

[17] A process for producing an aromatic nitrile compound according to [1], wherein the ammonia or ammonium salt is used in an amount at least equivalent to the raw material compound represented by the general formula (1).

BEST MODE FOR CARRYING OUT THE INVENTION

The present invention is described in detail below.

The process of the present invention is a process for producing an aromatic nitrile compound represented by the general formula (3), characterized in that one of an aromatic hydroxymethyl compound, an aromatic alkoxymethyl compound and an aromatic aldehyde compound, all represented by the general formula (1), or a mixture thereof [hereinafter, the compound or the mixture thereof may be expressed simply as "the raw material compound represented by the general formula (1)" or "the raw material compound"] is reacted with an oxidized bromine compound represented by the general formula (2) in the presence of an acid catalyst and either ammonia or an ammonium salt.

First, description is made on the raw material compound represented by the general formula (1), which is used as a raw material of the present invention process.

In the general formula (1), X is hydroxymethyl group; straight chain or branched chain alkoxymethyl group having 1 to 6 carbon atoms (hereinafter, the carbon atoms, when they are, for example, 1 to 6, are abbreviated as "C1 to C6"), such as methoxymethyl group, ethoxymethyl group or the like; or formyl group.

In the general formula (1), R is hydrogen atom; straight chain or branched chain C1 to C6 alkyl group such as methyl group, ethyl group, n-propyl group, isopropyl group, n-butyl group, sec-butyl group, t-butyl group, n-pentyl group, n-hexyl group or the like; hydroxyl group; straight chain or branched chain C1 to C6 alkoxy group such as methoxy group, ethoxy group, n-propoxy group, isopropoxy group or the like [the C1 to C6 alkoxy group may have substituents such as hydroxyl group, straight chain or branched chain C1 to C6 alkoxy group (e.g. methoxy group, ethoxy group, n-propoxy group, isopropoxy group), straight chain or branched chain C1 to C6 hydroxyalkyl group (e.g. hydroxymethyl group, hydroxyethyl group), straight chain or branched chain (C1 to C6 alkoxy)-(C1 to C6 alkyl) group (e.g. methoxymethyl group, methoxyethyl group, ethoxyethyl group), straight chain or branched chain C1 to C6 haloalkyl group (e.g. fluoromethyl group, difluoromethyl group, trifluoromethyl group), carboxyl group or metal salt thereof, straight chain or branched (C1 to C6 alkoxy) carbonyl group (e.g. methoxycarbonyl group, ethoxycarbonyl group), halogen atom (e.g. bromo, chloro, fluoro, iodo), nitro group, amino group, straight chain or branched chain mono- or di(C1 to C6 alkyl)amino group (e.g. methylamino group, dimethylamino group, ethylamino group, diethylamino group), straight chain or branched chain C1 to C6 alkylcarbonylamino group (e.g. acetylamino group, propionylamino group, butyrylamino group), cyano group, formyl group, straight chain or branched chain (C1 to C6 alkyl) carbonyl group (e.g. methylcarbonyl group, ethylcarbonyl group), and the like]; straight chain or branched chain C1 to C6 hydroxyalkyl group such as hydroxymethyl group, hydroxyethyl group or the like; straight chain or branched chain (C1 to C6 alkoxy)-(C1 to C6 alkyl) group such as methoxymethyl group, methoxyethyl group, ethoxyethyl group or the like; straight chain or branched chain C1 to C6 haloalkyl group such as fluoromethyl group, difluoromethyl group, trifluoromethyl group or the like; carboxyl group or metal salt thereof; straight chain or branched chain (C1 to C6 alkoxy)carbonyl group such as methoxycarbonyl group, ethoxycarbonyl group or the like; halogen atom such as bromo, chloro, fluoro, iodo or the like; nitro group; amino group; straight chain or branched chain mono- or di(C1 to C6 alkyl)amino group such as methyl amino group, dimethylamino group, ethylamino group, diethylamino group or the like; straight chain or branched chain (C1 to C6 alkyl) carbonylamino group such as acetylamino group, propionylamino group, butyrylamino group or the like; cyano group; formyl group; straight chain or branched chain (C1 to C6 alkyl)carbonyl group such as methylcarbonyl group, ethylcarbonyl group or the like; phenyl group [the phenyl group may have substituents such as straight chain or branched chain C1 to C6 alkyl group (e.g. methyl group, ethyl group, n-propyl group, isopropyl group, n-butyl group, sec-butyl group, t-butyl group, n-pentyl group, n-hexyl group), hydroxyl group, straight chain or branched chain C1 to C6 alkoxy group (e.g. methoxy group, ethoxy group, n-propoxy group, isopropoxy group), straight chain or branched chain C1 to C6 hydroxyalkyl group (e.g. hydroxymethyl group, hydroxyethyl group), straight chain or branched chain (C1 to C6 alkoxy)-(C1 to C6 alkyl) group (e.g. methoxymethyl group, methoxyethyl group, ethoxyethyl group), straight chain or branched chain C1 to C6 haloalkyl group (e.g. fluoromethyl group, difluoromethyl group, trifluoromethyl group), carboxyl group or metal salt thereof, straight chain or branched chain (C1 to C6 alkoxy)carbonyl group (e.g. methoxycarbonyl group, ethoxycarbonyl group), halogen atom (e.g. bromo, chloro, fluoro, iodo), nitro group, amino group, straight chain or branched chain mono- or di(C1 to C6 alkyl)amino group (e.g. methylamino group, dimethylamino group, ethylamino group, diethylamino group), straight chain or branched chain C1 to C6 alkylcarbonylamino group (e.g. acetylamino group, propionylamino group, butyrylamino group) cyano group, formyl group, straight chain or branched chain (C1 to C6 alkyl)carbonyl group (e.g. methylcarbonyl group, ethylcarbonyl group), and the like]; or hetero-aryl group such as pyridyl group, thienyl group, furyl group or the like [the hetero-aryl group may have substituents such as straight chain or branched chain C1 to C6 alkyl group (e.g. methyl group, ethyl group, n-propyl group, isopropyl group, n-butyl group, sec-butyl group, t-butyl group, n-pentyl group, n-hexyl group), hydroxyl group, straight chain or branched chain C1 to C6 alk-alkoxy group (e.g. methoxy group, ethoxy group, n-propoxy group, isopropoxy group), straight chain or branched chain C1 to C6 hydroxyalkyl group (e.g. hydroxymethyl group, hydroxyethyl group), straight chain or branched chain (C1 to C6 alkoxy)-(C1 to C6 alkyl) group (e.g. methoxymethyl group, methoxyethyl group, ethoxyethyl group), straight chain or branched chain C1 to C6 haloalkyl group (e.g. fluoromethyl group, difluoromethyl group, trifluoromethyl group), carboxyl group or metal salt thereof, straight chain or branched (C1 to C6 alkoxy)carbonyl group (e.g. methoxycarbonyl group, ethoxycarbonyl group), halogen atom (e.g. bromo, chloro, fluoro, iodo), nitro group, amino group, straight chain or branched chain mono- or di(C1 to C6 alkyl)amino group (e.g. methylamino group, dimethylamino group, ethylamino group, diethylamino group), straight chain or branched chain C1 to C6 alkylcarbonylamino group (e.g. acetylamino group, propionylamino group, butyrylamino group), cyano group, formyl group, straight chain or branched chain (C1 to C6 alkyl)carbonyl group (e.g. methylcarbonyl group, ethylcarbonyl group), and the like]. Two Rs may be bonded to each other to form a ring.

In the general formula (1), n is an integer of 1 to 9; q is an integer of 1 to 9; however, (q–n) is zero or a positive integer. When n is 2 or more, a plurality of Xs may be the same or different; similarly, when (q–n) is 2 or more, a plurality of Rs may be the same or different.

Incidentally, in the present invention, there is preferred a raw material compound wherein n is 1 to 3, in view of the availability of raw material compound and its reactivity.

Also in view of the availability of raw material compound and its reactivity, there are preferred a raw material compound wherein all of Rs are hydrogen atom or at least one of Rs is an electron-withdrawing group or an alkyl group and, in particular, a raw material compound wherein all Rs are hydrogen atom or at least one of Rs is a chloro group, a nitro group, a fluoro group or a methyl group.

In the compound represented by the general formula (1), usable in the present invention process, the ring A is an aromatic hetero-cycle having at least one hetero-atom, or a phenyl ring.

The hetero-cyclic aromatic hydroxymethyl compound, hetero-cyclic aromatic alkoxymethyl compound or hetero-cyclic aromatic aldehyde compound wherein the ring A is an aromatic hetero-cycle having at least one hetero-atom, may be a mono-cyclic compound or a condensed ring compound as long as it is a hetero-cyclic compound having aromaticity. There can preferably be mentioned a hetero-cyclic aromatic compound wherein the ring A has at least one hetero-atom selected from the group consisting of nitrogen atom, oxygen atom and sulfur atom; more preferably a hetero-cyclic aromatic compound which has 1 to 3 hetero-atoms selected from the group consisting of nitrogen atom, oxygen atom and sulfur atom and which is 5- to 10-membered in total. Specifically, there is preferred a hetero-cyclic aromatic compound of 2 to 9 carbon atoms having 1 to 3 same or different hetero-atoms selected from the above-mentioned hetero-atom group; and there is particularly preferred a hetero-cyclic aromatic compound of 2 to 9 carbon atoms having 1 to 2 same or different hetero-atoms selected from the above-mentioned hetero-atom group, such as furan ring, thiophene ring, pyridine ring, quinoline ring or thiazole ring.

There can specifically be mentioned mono-cyclic or condensed ring aromatic hetero-cyclic compounds such as pyridine (e.g. 2-hydroxymethylpyridine, 3-hydroxymethylpyridine, 4-hydroxymethylpyridine, 2-methoxymethylpyridine, 3-methoxymethylpyridine, 4-methoxymethylpyridine, 2-formylpyridine, 3-formylpyridine, 4-formylpyridine), quinoline (e.g. 2-hydroxymethylquinoline, 3-hydroxymethylquinoline, 4-hydroxymethylquinoline, 2-methoxymethylquinoline, 3-methoxymethylquinoline, 4-methoxymethylquinoline, quinoline-2-carboaldehyde, quinoline-3-carboaldehyde, quinoline-4-carboaldehyde, 5-hydroxymethylquinoline, 6-hydroxymethylquinoline, 7-hydroxymethylquinoline, 8-hydroxymethylquinoline, 5-methoxymethylquinoline, 6-methoxymethylquinoline, 7-methoxymethylquinoline, 8-methoxymethylquinoline), isoquinoline (e.g. 1-hydroxymethylisoquinoline, 3-hydroxymethylisoquinoline, 4-hydroxymethylisoquinoline, 2-methoxymethylisoquinoline, 3-methoxymethylisoquinoline, 4-methoxymethylisoquinoline, isoquinoline-1-carboaldehyde, isoquinoline-3-carboaldehyde, isoquinoline-4-carboaldehyde, 5-hydroxymethylisoquinoline, 6-hydroxymethylisoquinoline, 7-hydroxymehtylisoquinoline, 8-hydroxymethylisoquinoline, 5-methoxymethylisoquinoline, 6-methoxymethylisoquinoline, 7-methoxymethylisoquinoline, 8-methoxymethylisoquinoline), pyridazine (3-hydroxymethylpyridazine, 4-hydroxymethylpyridazine, 3-methoxymethylpyridazine, 4-methoxymethylpyridazine, 3-formylpyridazine, 4-formylpyridazine), pyrazine (e.g. 2-hydroxymethylpyrazine, 2-methoxymethylpyrazine, 2-formylpyrazine), triazine (e.g. 2-hydroxymethyl-1,3,5-triazine, 2-methoxymethyl-1,3,5-triazine, 2-formyl-1,3,5-triazine), thiophene (e.g. 2-hydroxymethylthiophene, 3-hydroxymethylthiophene, 4-hydroxymethylthiophene, 2-methoxymethylthiophene, 3-methoxymethylthiophene, 4-methoxymethylthiophene, 2-formylthiophene, 3-formylthiophene, 4-formylthiophene, 2-formyl-5-methylthiophene), furan (e.g. 2-hydroxymehtylfuran, 3-hydroxymehtylfuran, 4-hydroxymethylfuran, 2-methoxymethylfuran, 3-methoxymethyluran, 4-methoxymethylfuran, 2-formuylfuran, 3-formylfuran, 4-formylfuran), pyrrole (e.g. 2-hydroxymethylpyrrole, 3-hydroxymethylpyrrole, 4-hydroxymethylpyrrole, 2-methoxymethylpyrrole, 3-methoxymethylpyrrole, 4-methoxymethylpyrrole, 2-formylpyrrole, 3-formylpyrrole, 4-formylpyrrole), pyrazole (e.g. 3-hydroxymethylpyrazole, 4-hydroxymethylpyrazole, 5-hydroxymethylpyrazole, 3-methoxymethylpyrazole, 4-methoxymethylpyrazole, 5-methoxymethylpyrazole, 3-formylpyrazole, 4-formylpyrazole, 5-formylpyrazole), imidazole (e.g. 2-hydroxymethylimidazole, 4-hydroxymethylimidazole, 5-hydroxymethylimidazole, 2-methoxymethylimidazole, 4-methoxymethylimidazole, 5-methoxymethylimidazole, 2-formylimidazole, 4-formylimidazole, 5-formylimidazole), triazole (e.g. 3-hydroxymethyl-1,2,4-triazole, 5-hydroxymethyl-1,2,4-triazole, 3-methoxymethyl-1,2,4-triazole, 5-methoxymethyl-1,2,4-triazole, 3-formyl-1,2,4-triazole), tetrazole (e.g. 5-hydroxymethyl-1H-tetrazole, 5-methoxymehtyl-1H-tetrazole, 5-formyl-1H-tetrazole), oxazole (e.g. 2-hydroxymethyloxazole, 4-hydroxymethyloxazole, 5-hydroxymethyloxazole, 2-methoxymethyloxazole, 4-methoxymethyloxazole, 5-methoxymethyloxazole, 2-formyloxazole, 4-formyloxazole, 5-formyloxazole), thiazole (e.g. 2-hydroxymehtylthiazole, 4-hydroxymehtylthiazole, 5-hydroxymehtylthiazole, 2-methoxymethylthiazole, 4-methoxymethylthiazole, 5-methoxymethylthiazole, 2-formylthiazole, 4-formylthiazole, 5-formylthiazole), isoxazole (e.g. 3-hydroxymethylisoxazole, 4-hydroxymethylisoxazole, 5-hydroxymethylisoxazole, 3-methoxymethylisoxazole, 4-methoxymethylisoxazole, 5-methoxymethylisoxazole, 3-formylisoxazole, 4-formylisoxazole, 5-formylisoxazole), isothiazole (e.g. 3-hydroxymethylisothiazole, 4-hydroxymethylisothiazole, 5-hydroxymethylisothiazole, 3-methoxymethylisothiazole, 4-methoxymethylisothiazole, 5-methoxymethylisothiazole, 3-formylisothiazole, 4-formylisothiazole, 5-formylisothiazole), thiadiazole (e.g. 4-hydroxymethyl-1,2,3-thiadiazole, 5-hydroxymethyl-1,2,3-thiadiazole, 4-methoxymethyl-1,2,3-thiadiazole, 5-methoxymethyl-1,2,3-thiadiazole, 4-formyl-1,2,3-thiadiazole, 5-formyl-1,2,3-thiadiazole, 3-hydroxymethyl-1,2,4-thiadiazole, 5-hydroxymehtyl-1,2,4-thiadiazole, 3-methoxymethyl-1,2,4-thiadiazole, 5-methoxymethyl-1,2,4-thiadiazole, 3-formyl-1,2,4-thiadiazole, 5-formyl-1,2,4-thiadiazole, 2-hyroxymethyl-1,3,4-thiadiazole, 5-hydroxymethyl-1,3,4-thiadiazole, 2-methoxymethyl-1,3,4-thiadiazole, 5-methoxymethyl-1,3,4-thiadiazole, 2-formyl-1,3,4-thiadiazole, 5-formyl-1,3,4-thiadiazole), indole (e.g. 2-hydroxymethylindole, 3-hydroxymethylindole, 4-hydroxymehtylindole, 5-hydroxymethylindole, 6-hydroxymethylindole, 7-hydroxymethylindole, 2-methoxymethylindole, 3-methoxymethylindole, 4-methoxymethylindole, 5-methoxymethylindole, 6-methoxymethylindole, 7-methoxymethylindole, 2-formylindole, 3-formylindole, 4-formylindole; 5-formylindole, 6-formylindole, 7-formylindole), benzothiophene (e.g. 2-hydroxymethylbenzothiophene, 3-hydroxymethylbenzothiophene, 4-hydroxymethylbenzothiophene, 5-hydroxymethylbenzothiophene, 6-hydroxymethylbenzothiophene, 7-hydroxymethylbenzothiophene, 2-methoxymethylbenzothiophene, 3-methoxymethylbenzothiophene, 4-methoxymethylbenzothiophene, 5-methoxymethylbenzothiophene, 6-methoxymethylbenzothiophene, 7-methoxymethylbenzothiophene, 2-formylbenzothiophene, 3-formylbenzothiophene, 4-formylbenzothiophene, 5-formylbenzothiophene, 6-formylbenzothiophene, 7-formylbenzothiophene), pyrimidine (e.g. 2-hydroxymethyl-1,3-pyrimidine, 4-hydroxymethyl-1,3-pyrimidine, 5-hydroxymethyl-1,3-pyrimidine, 2-methoxymethyl-1,3-pyrimidine, 4-methoxymethyl-1,3-pyrimidine, 5-methoxymethyl-1,3-pyrimidine, 2-formyl-1,3-pyrimidine, 4-formyl-1,3-pyrimidine, 5-formyl-1,3-pyrimidine) and the like.

The hetero-cyclic aromatic compound of the general formula (1) may have, as R, substituents such as straight chain or branched chain C1 to C6 alkyl group such as methyl group, ethyl group, n-propyl group, isopropyl group, n-butyl group, sec-butyl group, t-butyl group, n-pentyl group, n-hexyl group or the like; hydroxyl group; straight chain or branched chain C1 to C6 alkoxy group such as methoxy group, ethoxy group, n-propoxy group, isopropoxy group or the like [the C1 to C6 alkoxy group may have substituents such as hydroxyl group, straight chain or branched chain C1 to C6 alkoxy group (e.g. methoxy group, ethoxy group, n-propoxy group, isopropoxy group), straight chain or branched chain C1 to C6 hydroxyalkyl group (e.g. hydroxymethyl group, hydroxyethyl group), straight chain or branched chain (C1 to C6 alkoxy)-(C1 to C6 alkyl) group (e.g. methoxymethyl group, methoxyethyl group, ethoxyethyl group), straight chain or branched chain C1 to C6 haloalkyl group (e.g. fluoromethyl group, difluoromethyl group, trifluoromethyl group), carboxyl group or metal salt thereof, straight chain or branched chain (C1 to C6 alkoxy) carbonyl group (e.g. methoxycarbonyl group, ethoxycarbonyl group), halogen atom (e.g. bromo, chloro, fluoro, iodo), nitro group, amino group, straight chain or branched chain mono- or di(C1 to C6 alkyl)amino group (e.g. methylamino group, dimethylamino group, ethylamino group, diethylamino group), straight chain or branched chain. C1 to C6 alkylcarbonylamino group (e.g. acetylamino group, propionylamino group, butyrylamino group), cyano group, formyl group, straight chain or branched chain (C1 to C6 alkyl) carbonyl group (e.g. methylcarbonyl group, ethylcarbonyl group), and the like]; straight chain or branched chain C1 to C6 hydroxyalkyl group such as hydroxymethyl group, hydroxyethyl group or the like; straight chain or branched chain (C1 to C6 alkoxy)-(C1 to C6 alkyl) group such as methoxymethyl group, methoxyethyl group, ethoxyethyl group or the like; straight chain or branched chain C1 to C6 haloalkyl group such as fluoromethyl group, difluoromethyl group, trifluoromethyl group or the like; carboxyl group or metal salt thereof; straight chain or branched chain (C1 to C6 alkoxy)carbonyl group such as methoxycarbonyl group, ethoxycarbonyl group or the like; halogen atom such as bromo, chloro, fluoro, iodo or the like; nitro group; amino group; straight chain or branched chain mono- or di(C1 to C6 alkyl)amino group such as methyl amino group, dimethylamino group, ethylamino group, diethylamino group or the like; straight chain or branched chain (C1 to C6 alkyl) carbonylamino group such as acetylamino group, propionylamino group, butyrylamino group or the like; cyano group; formyl group; straight chain or branched chain (C1 to C6 alkyl)carbonyl group such as methylcarbonyl group, ethylcarbonyl group or the like; phenyl group [the phenyl group may have substituents such as straight chain or branched chain C1 to C6 alkyl group (e.g. methyl group, ethyl group, n-propyl group, isopropyl group, n-butyl group, sec-butyl group, t-butyl group, n-pentyl group, n-hexyl group), hydroxyl group, straight chain or branched chain C1 to C6 alkoxy group (e.g. methoxy group, ethoxy group, n-propoxy group, isopropoxy group), straight chain or branched chain C1 to C6 hydroxyalkyl group (e.g. hydroxymethyl group, hydroxyethyl group), straight chain or branched chain (C1 to C6 alkoxy)-(C1 to C6 alkyl) group (e.g. methoxymethyl group, methoxyethyl group, ethoxyethyl group), straight chain or branched chain C1 to C6 haloalkyl group (e.g. fluoromethyl group, difluoromethyl group, trifluoromethyl group), carboxyl group or metal salt thereof, straight chain or branched chain (C1 to C6 alkoxy)carbonyl group (e.g. methoxycarbonyl group, ethoxycarbonyl group), halogen atom (e.g. bromo; chloro, fluoro, iodo), nitro group, amino group, straight chain or branched chain mono- or di(C1 to C6 alkyl)amino group (e.g. methylamino group, dimethylamino group, ethylamino group, diethylamino group), straight chain or branched chain C1 to C6 alkylcarbonylamino group (e.g. acetylamino group, propionylamino group, butyrylamino group), cyano group, formyl group, straight chain or branched chain (C1 to C6 alkyl)carbonyl group (e.g. methylcarbonyl group, ethylcarbonyl group), and the like]; hetero-aryl group such as pyridyl group, thienyl group, furyl group or the like [the hetero-aryl group may have substituents such as straight chain or branched chain C1 to C6 alkyl group (e.g. methyl group, ethyl group, n-propyl group, isopropyl group, n-butyl group, sec-butyl group, t-butyl group, n-pentyl group, n-hexyl group), hydroxyl group, straight chain or branched chain C1 to C6 alkoxy group (e.g. methoxy group, ethoxy group, n-propoxy group, isopropoxy group), straight chain or branched chain C1 to C6 hydroxyalkyl group (e.g. hydroxymethyl group, hydroxyethyl group), straight chain or branched chain (C1 to C6 alkoxy)-(C1 to C6 alkyl) group (e.g. methoxymethyl group, methoxyethyl group, ethoxyethyl group), straight chain or branched chain C1 to C6 haloalkyl group (e.g. fluoromethyl group, difluoromethyl group, trifluoromethyl group), carboxyl group or metal salt thereof, straight chain or branched (C1 to C6 alkoxy)carbonyl group (e.g. methoxycarbonyl group, ethoxycarbonyl group), halogen atom (e.g. bromo, chloro, fluoro, iodo), nitro group, amino group, straight chain or branched chain mono- or di(C1 to C6 alkyl)amino group (e.g. methylamino group, dimethylamino group, ethylamino group, diethylamino group), straight chain or branched chain C1 to C6 alkylcarbonylamino group (e.g. acetylamino group, propionylamino group, butyrylamino group), cyano group, formyl group, straight chain or branched chain (C1 to C6 alkyl)carbonyl group (e.g. methylcarbonyl group, ethylcarbonyl group), and the like]; and the like.

The hetero-cyclic aromatic hydroxymethyl compound, hetero-cyclic aromatic alkoxymethyl compound or hetero-cyclic aromatic aldehyde compound is a known compound, or can be produced, for example, by a method which comprises hydrolyzing a corresponding hetero-cyclic aromatic chloromethyl compound (a raw material) in water, a method which comprises reacting a corresponding hetero-cyclic aromatic chloromethyl compound with a metal alkoxide (e.g. sodium alkoxide) in an appropriate solvent, or a method which comprises hydrolyzing a corresponding hetero-cyclic aromatic dichloromethyl compound (a raw material) in water.

In the present invention, the hetero-cyclic aromatic hydroxymethyl compound, hetero-cyclic aromatic alkoxymethyl compound or hetero-cyclic aromatic aldehyde compound which is a raw material, may be used as a mixture thereof and not as a single substance.

As the benzyl alcohol compound, benzyl ether compound or benzaldehyde compound when the ring A is a phenyl ring, there can specifically be mentioned benzyl alcohol compounds which may have, as the substituent R, straight chain or branched chain C1 to C6 alkyl group, hydroxyl group, straight chain or branched chain C1 to C6 alkoxy group [the C1 to C6 alkoxy group may have substituents such as hydroxyl group, straight chain or branched chain C1 to C6 alkoxy group (e.g. methoxy group, ethoxy group, n-propoxy group, isopropoxy group), straight chain or branched chain C1 to C6 hydroxyalkyl group (e.g. hydroxymethyl group, hydroxyethyl group), straight chain or branched chain (C1 to C6 alkoxy)-(C1 to C6 alkyl) group (e.g. methoxymethyl group, methoxyethyl group, ethoxyethyl group), straight chain or branched chain C1 to C6 haloalkyl group (e.g. fluoromethyl group, difluoromethyl group, trifluoromethyl group), carboxyl group or metal salt thereof, straight chain or branched (C1 to C6 alkoxy)carbonyl group (e.g. methoxycarbonyl group, ethoxycarbonyl group), halogen atom (e.g. bromo, chloro, fluoro, iodo), nitro group, amino group, straight chain or branched chain mono- or di(C1 to C6 alkyl)amino group (e.g. methylamino group, dimethylamino group, ethylamino group, diethylamino group), straight chain or branched chain C1 to C6 alkylcarbonylamino group (e.g. acetylamino group, propionylamino group, butyrylamino group), cyano group, formyl group, straight chain or branched chain (C1 to C6 alkyl)carbonyl group (e.g. methylcarbonyl group, ethylcarbonyl group), and the like], straight chain or branched chain hydroxy-(C1 to C6) alkyl group, straight chain or branched chain (C1 to C6 alkoxy)-(C1 to C6 alkyl) group, straight chain or branched chain C1 to C6 haloalkyl group, carboxyl group or metal salt thereof, straight chain or branched chain (C1 to C6 alkoxy)carbonyl group, halogen atom, nitro group, amino group, straight chain or branched chain mono- or di(C1 to C6 alkyl)amino group, straight chain or branched chain (C1 to C6 alkyl) carbonylamino group, cyano group, formyl group, straight chain or branched chain (C1 to C6 alkyl)carbonyl group, phenyl group [the phenyl group may have substituents such as straight chain or branched chain C1 to C6 alkyl group, hydroxyl group, straight chain or branched chain C1 to C6 alkoxy group, straight chain or branched chain C1 to C6 hydroxyalkyl group, straight chain or branched chain (C1 to C6 alkoxy)-(C1 to C6 alkyl) group, straight chain or branched chain C1 to C6 haloalkyl group, carboxyl group or metal salt thereof, straight chain or branched chain (C1 to C6 alkoxy)carbonyl group, halogen atom, nitro group, amino group, straight chain or branched chain mono- or di(C1 to C6 alkyl)amino group, straight chain or branched chain C1 to C6 alkylcarbonylamino group, cyano group, formyl group, straight chain or branched chain (C1 to C6 alkyl) carbonyl group, and the like], hetero-aryl group (e.g. pyridyl group, thienyl group, furyl group) [the hetero-aryl group may have substituents such as straight chain or branched chain C1 to C6 alkyl group (e.g. methyl group, ethyl group, n-propyl group, iso-propyl group, n-butyl group, sec-butyl group, t-butyl group, n-pentyl group, n-hexyl group), hydroxyl group, straight chain or branched chain C1 to C6 alkoxy group (e.g. methoxy group, ethoxy group, n-propoxy group, isopropoxy group), straight chain or branched chain C1 to C6 hydroxyalkyl group (e.g. hydroxymethyl group, hydroxyethyl group), straight chain or branched chain (C1 to C6 alkoxy)-(C1 to C6 alkyl) group (e.g. methoxymethyl group, methoxyethyl group, ethoxyethyl group), straight chain or branched chain C1 to C6 haloalkyl group (e.g. fluoromethyl group, difluoromethyl group, trifluoromethyl group), carboxyl group or metal salt thereof, straight chain or branched chain (C1 to C6 alkoxy)carbonyl group (e.g. methoxycarbonyl group, ethoxycarbonyl group), halogen atom (e.g. bromo, chloro, fluoro, iodo), nitro group, amino group, straight chain or branched chain mono- or di(C1 to C6 alkyl)amino group (e.g. methylamino group, dimethylamino group; ethylamino group, diethylamino group), straight chain or branched chain C1 to C6 alkylcarbonylamino group (e.g. acetylamino group, propionylamino group, butyrylamino group), cyano group, formyl group, straight chain or branched chain (C1 to C6 alkyl)carbonyl group (e.g. methylcarbonyl group, ethylcarbonyl group), and the like], and like, typified by benzyl alcohol, o-hydroxymethyltoluene, m-hydroxymethyltoluene, p-hydroxymethyltoluene, o-hydroxymethylphenol, m-hydroxymethylphenol, p-hydroxymethylphenol, o-methoxybenzyl alcohol, m-methoxybenzyl alcohol, p-methoxybenzyl alcohol, o-xylylene glycol, m-xylylene glycol, p-xylylene glycol, o-fluoromethylbenzyl alcohol, m-fluoromethylbenzyl alcohol, p-fluoromethylbenzyl alcohol, o-hydroxymethylbenzoic acid, m-hydroxymethylbenzoic acid, p-hydroxymethylbenzoic acid, methyl o-hydroxymethylbenzoate, methyl m-hydroxymethylbenzoate, methyl p-hydroxymethylbenzoate, o-chlorobenzyl alcohol, m-chlorobenzyl alcohol, p-chlorobenzyl alcohol, o-nitrobenzyl alcohol, m-nitrobenzyl alcohol, p-nitrobenzyl alcohol, o-hydroxymehtylaniline, m-hydroxymehtylaniline, p-hydroxymehtylaniline; N-methyl-o-hydroxymethylaniline, N-methyl-m-hydroxymethylaniline, N-methyl-p-hydroxymethylaniline, N,N-dimethyl-o-hydroxymethylaniline, N,N-dimethyl-m-hydroxymethylaniline, N,N-dimethyl-p-hydroxymethylaniline, o-hydroxymethylacetanilide, m-hydroxymethylacetanilide, p-hydroxymethylacetanilide, o-cyanobenzyl alcohol, m-cyanobenzyl alcohol, p-cyanobenzyl alcohol, o-hydroxymethylbenzaldehyde, m-hydroxymethylbenzaldehyde, p-hydroxymethylbenzaldehyde, o-hydroxymethylacetophenone, m-hydroxymethylacetophenone, p-hydroxymethylacetophenone, 2-hydroxymethylbiphenyl, 3-hydroxymethylbiphenyl, 4-hydroxymethylbiphenyl, 4,4'-dihydroxymethylbiphenyl, o-hydroxymethyl-benzylamine, m-hydroxymethyl-benzylamine, p-hydroxymethyl-benzylamine, etc.; benzyl ether compounds which may have, as the substituent R, straight chain or branched chain C1 to C6 alkyl group, hydroxyl group, straight chain or branched chain C1 to C6 alkoxy group [the C1 to C6 alkoxy group may have substituents such as hydroxyl group, straight chain or branched chain C1 to C6 alkoxy group (e.g. methoxy group, ethoxy group, n-propoxy group, isopropoxy group) straight chain or branched chain C1 to C6 hydroxyalkyl group (e.g. hydroxymethyl group, hydroxyethyl group), straight chain or branched chain (C1 to C6 alkoxy)-(C1 to C6 alkyl) group (e.g. methoxymethyl group, methoxyethyl group, ethoxyethyl group), straight chain or branched chain C1 to C6 haloalkyl group (e.g. fluoromethyl group, difluoromethyl group, trifluoromethyl group), carboxyl group or metal salt thereof, straight chain or branched (C1 to C6 alkoxy) carbonyl group (e.g. methoxycarbonyl group, ethoxycarbonyl group), halogen atom (e.g. bromo, chloro, fluoro, iodo), nitro group, amino group, straight chain or branched chain mono- or di(C1 to C6 alkyl)amino group (e.g. methylamino group, dimethylamino group, ethylamino group, diethylamino group), straight chain or branched chain C1 to C6 alkylcarbonylamino group (e.g. acetylamino group, propionylamino group, butyrylamino group), cyano group, formyl group, straight chain or branched chain (C1 to C6 alkyl) carbonyl group (e.g. methylcarbonyl group, ethylcarbonyl group), and the like], straight chain or branched chain hydroxy-(C1 to C6) alkyl group, straight chain or branched chain (C1 to C6 alkoxy)-(C1 to C6 alkyl) group, straight chain or branched chain C1 to C6 haloalkyl group, carboxyl group or metal salt thereof, straight chain or branched chain (C1 to C6 alkoxy)carbonyl group, halogen atom, nitro group, amino group, straight chain or branched chain mono- or di(C1 to C6 alkyl)amino group, straight chain or branched chain (C1 to C6 alkyl)carbonylamino group, cyano group, formyl group, straight chain or branched chain (C1 to C6 alkyl)carbonyl group, phenyl group [the phenyl group may have substituents such as straight chain or branched chain C1 to C6 alkyl group, hydroxyl group, straight chain or branched chain C1 to C6 alkoxy group, straight chain or branched chain C1 to C6 hydroxyalkyl group, straight chain or branched chain (C1 to C6 alkoxy)-(C1 to C6 alkyl) group, straight chain or branched chain C1 to C6 haloalkyl group, carboxyl group or metal salt thereof, straight chain or branched chain (C1 to C6 alkoxy)carbonyl group, halogen atom, nitro group, amino group, straight chain or branched chain mono- or di(C1 to C6 alkyl)amino group, straight chain or branched chain C1 to C6 alkylcarbonylamino group, cyano group, formyl group, straight chain or branched chain (C1 to C6 alkyl)carbonyl group, and the like], hetero-aryl group (e.g. pyridyl group, thienyl group, furyl group) [the hetero-aryl group may have substituents such as straight chain or branched chain C1 to C6 alkyl group (e.g. methyl group, ethyl group, n-propyl group, isopropyl group, n-butyl group, sec-butyl group, t-butyl group, n-pentyl group, n-hexyl group), hydroxyl group, straight chain or branched chain C1 to C6 alkoxy group (e.g. methoxy group, ethoxy group, n-propoxy group, isopropoxy group), straight chain or branched chain C1 to C6 hydroxyalkyl group (e.g. hydroxymethyl group, hydroxyethyl group), straight chain or branched chain (C1 to C6 alkoxy)-(C1 to C6 alkyl) group (e.g. methoxymethyl group, methoxyethyl group, ethoxyethyl group), straight chain or branched chain C1 to C6 haloalkyl group (e.g. fluoromethyl group, difluoromethyl group, trifluoromethyl group), carboxyl group or metal salt thereof, straight chain or branched chain (C1 to C6 alkoxy)carbonyl group (e.g. methoxycarbonyl group, ethoxycarbonyl group), halogen atom (e.g. bromo, chloro, fluoro, iodo), nitro group, amino group, straight chain or branched chain mono- or di(C1 to C6 alkyl)amino group (e.g. methylamino group, dimethylamino group, ethylamino group, diethylamino group), straight chain or branched chain C1 to C6 alkylcarbonylamino group (e.g. acetylamino group, propionylamino group, butyrylamino group), cyano group, formyl group, straight chain or branched chain (C1 to C6 alkyl)carbonyl group (e.g. methylcarbonyl group, ethylcarbonyl group), and the like], and the like, typified by methoxymethylbenzene, o-methoxymethyltoluene, m-methoxymethyltoluene, p-methoxymethyltoluene, o-methoxymethylphenol, m-methoxymethylphenol, p-methoxymethylphenol, o-methoxymethoxymethylbenzene, m-methoxymethoxymethylbenzene, p-methoxymethoxymethylbenzene, o-xylylene glycol dimethyl ether, m-xylylene glycol dimethyl ether, p-xylylene glycol dimethyl ether, o-methoxymethylfluoromethylbenzene, m-methoxymethyl-fluoromethylbenzene, p-methoxymethyl-fluoromethylbenzene, o-methoxymethylbenzoic acid, m-methoxymethylbenzoic acid, p-methoxymethylbenzoic acid, methyl o-methoxymethylbenzoate, methyl m-methoxymethylbenzoate, methyl p-methoxymethylbenzoate, o-chlorobenzyl methyl ether, m-chlorobenzyl methyl ether, p-chlorobenzyl methyl ether, o-nitrobenzyl methyl ether, m-nitrobenzyl methyl ether, p-nitrobenzyl methyl ether, o-methoxymethylaniline, m-methoxymethylaniline, p-methoxymethylaniline, N-methyl-o-methoxymethylaniline, N-methyl-m-methoxymethylaniline, N-methyl-p-methoxymehtylaniline, o-methoxymethylacetoanilide, m-methoxymethylacetoanilide, p-methoxymethylacetoanilide, o-cyanobenzyl methyl ether, m-cyanobenzyl methyl ether, p-cyanobenzyl methyl ether, o-methoxymethylacetophenone, m-methoxymethylacetophenone, p-methoxymethylacetophenone, 2-methoxymethylbiphenyl, 3-methoxymethylbiphenyl, 4-methoxymethylbiphenyl, 4,4'dimethoxymethylbiphenyl, o-methoxymethyl-benzylamine, m-methoxymethyl-benzylamine, p-methoxymethyl-benzylamine, etc.; benzaldehyde compounds which may have, as the substituent R, straight chain or branched chain C1 to C6 alkyl group, hydroxyl group, straight chain or branched chain C1 to C6 alkoxy group [the C1 to C6 alkoxy group may have substituents such as hydroxyl group, straight chain or branched chain C1 to C6 alkoxy group (e.g. methoxy group, ethoxy group, n-propoxy group, isopropoxy group), straight chain or branched chain C1 to C6 hydroxyalkyl group (e.g. hydroxymethyl group, hydroxyethyl group), straight chain or branched chain (C1 to C6 alkoxy)-(C1 to C6 alkyl) group (e.g. methoxymethyl group, methoxyethyl group, ethoxyethyl group), straight chain or branched chain C1 to C6 haloalkyl group (e.g. fluoromethyl group, difluoromethyl group, trifluoromethyl group), carboxyl group or metal salt thereof, straight chain or branched (C1 to C6 alkoxy) carbonyl group (e.g. methoxycarbonyl group, ethoxycarbonyl group), halogen atom (e.g. bromo, chloro, fluoro, iodo), nitro group, amino group, straight chain or branched chain mono- or di(C1 to C6 alkyl)amino group (e.g. methylamino group, dimethylamino group, ethylamino group, diethylamino group), straight chain or branched chain C1 to C6 alkylcarbonylamino group (e.g. acetylamino group, propionylamino group, butyrylamino group), cyano group, formyl group, straight chain or branched chain (C1 to C6 alkyl) carbonyl group (e.g. methylcarbonyl group, ethylcarbonyl group), and the like], straight chain or branched chain hydroxy-(C1 to C6) alkyl group, straight chain or branched chain (C1 to C6 alkoxy)-(C1 to C6 alkyl) group, straight chain or branched chain C1 to C6 haloalkyl group, carboxyl group or metal salt thereof, straight chain or branched chain (C1 to C6 alkoxy)carbonyl group, halogen atom, nitro group, amino group, straight chain or branched chain mono- or di(C1 to C6 alkyl)amino group, straight chain or branched chain (C1 to C6 alkyl)carbonylamino group, cyano group, formyl group, straight chain or branched chain (C1 to C6 alkyl)carbonyl group, phenyl group [the phenyl group may have substituents such as straight chain or branched chain C1 to C6 alkyl group, hydroxyl group, straight chain or branched chain C1 to C6 alkoxy group, straight chain or branched chain C1 to C6 hydroxyalkyl group, straight chain or branched chain (C1 to C6 alkoxy)-(C1 to C6 alkyl) group, straight chain or branched chain C1 to C6 haloalkyl group, carboxyl group or metal salt thereof, straight chain or branched chain (C1 to C6 alkoxy)carbonyl group, halogen atom, nitro group, amino group, straight chain or branched chain mono- or di(C1 to C6 alkyl)amino group, straight chain or branched chain C1 to C6 alkylcarbonylamino group, cyano group, formyl group, straight chain or branched chain (C1 to C6 alkyl) carbonyl group, and the like], hetero-aryl group (e.g. pyridyl group, thienyl group, furyl group) [the hetero-aryl group may have substituents such as straight chain or branched chain C1 to C6 alkyl group (e.g. methyl group, ethyl group, n-propyl group, isopropyl group, n-butyl group, sec-butyl group, t-butyl group, n-pentyl group, n-hexyl group), hydroxyl group, straight chain or branched chain C1 to C6 alkoxy group (e.g. methoxy group, ethoxy group, n-propoxy group, isopropoxy group), straight chain or branched chain C1 to C6 hydroxyalkyl group (e.g. hydroxymethyl group, hydroxyethyl group), straight chain or branched chain (C1 to C6 alkoxy)-(C1 to C6 alkyl) group (e.g. methoxymethyl group, methoxyethyl group, ethoxyethyl group), straight chain or branched chain C1 to C6 haloalkyl group (e.g. fluoromethyl group, difluoromethyl group, trifluoromethyl group), carboxyl group or metal salt thereof, straight chain or branched chain (C1 to C6 alkoxy)carbonyl group (e.g. methoxycarbonyl group, ethoxycarbonyl group), halogen atom (e.g. bromo, chloro, fluoro, iodo), nitro group, amino group, straight chain or branched chain mono- or di(C1 to C6 alkyl)amino group (e.g. methylamino group, dimethylamino group, ethylamino group, diethylamino group), straight chain or branched chain C1 to C6 alkylcarbonylamino group (e.g. acetylamino group, propionylamino group, butyrylamino group), cyano group, formyl group, straight chain or branched chain (C1 to C6 alkyl)carbonyl group (e.g. methylcarbonyl group, ethylcarbonyl group), and the like], and the like, typified by benzaldehyde, o-methylbenzaldehyde, m-methylbenzaldehyde, p-methylbenzaldehyde, o-formylphenol, m-formylphenol, p-formylphenol, o-methoxybenzaldehyde, m-methoxybenzaldehyde, p-methoxybenzaldehyde, o-aminomethylbenzaldehyde, m-aminomethylbenzaldehyde, p-aminomethylbenzaldehyde, o-fluoromethyl-benzaldehyde, m-fluoromethyl-benzaldehyde, p-fluoromethyl-benzaldehyde, o-formylbenzoic acid, m-formylbenzoic acid, p-formylbenzoic acid, methyl o-formylbenzoate, methyl m-formylbenzoate, methyl p-formylbenzoate, o-chlorobenzaldehyde, m-chlorobenzaldehyde, p-chlorobenzaldehyde, o-nitrobenzaldehyde, m-nitrobenzaldehyde, p-nitrobenzaldehyde, o-formylaniline, m-formylaniline, p-formylaniline, N-methyl-o-formylaniline, N-methyl-m-formylaniline, N-methyl-p-formylaniline, o-formylacetoanilide, m-formylacetoanilide, p-formylacetoanilide, o-cyanobenzaldehyde, m-cyanobenzaldehyde, p-cyanobenzaldehyde, o-phthalaldehyde, m-phthalaldehyde, p-phthalaldehyde, o-formylacetophenone, m-formylacetophenone, p-formylacetophenone, 2-formylbiphenyl, 3-formylbiphenyl, 4-formylbiphenyl, 4,4'diformylbiphenyl, etc.; and benzyl alcohol compounds, benzyl ether compounds and benzaldehyde compounds, such as o-xylylene glycol monomethyl ether, m-xylylene glycol monomethyl ether, p-xylylene glycol monomethyl ether, o-methoxymethylbenzaldehyde, m-methoxymethylbenzaldehyde, p-methoxymethylbenzaldehyde, o-hydroxymethylbenzaldehyde, m-hydroxymethylbenzaldehyde, p-hydroxymethylbenzaldehyde, o-methoxymethylbenzaldehyde, m-methoxymethylbenzaldehyde, p-methoxymethylbenzaldehyde and the like.

The benzyl alcohol compound, benzyl ether compound or benzaldehyde compound is a known compound, or can be produced, for example, by a method which comprises hydrolyzing a corresponding benzyl chloride compound as a raw material in water, a method which comprises reacting a corresponding benzyl chloride compound with a metal alkoxide (e.g. sodium alkoxide) in an appropriate solvent, a method which comprises hydrolyzing a corresponding benzyl chloride compound as a raw material in water, or a method which comprises conducting alcoholysis of a benzyl chloride compound.

In the present invention process, it is also possible that, in production of the raw material compound, corresponding toluene, for example, is chlorinated to obtain a mixture of corresponding chlorotoluene derivatives (generally, a mixture of a benzyl chloride compound, a benzyl chloride compound, etc.) and the mixture per se is hydrolyzed in water or decomposed in an alcohol to produce a mixture of a corresponding benzyl alcohol compound, a benzyl ether compound and a benzaldehyde compound (i.e. a raw material compound comprising a plurality of kinds of compounds) and this mixture itself is used as a raw material of the present invention process without purifying it to obtain a single product of a benzyl alcohol compound, a benzyl ether compound or a benzaldehyde compound.

Successively, description is made on the oxidized bromine compound represented by the general formula (2).

In the general formula (2), M is a hydrogen atom, or a metal atom of alkali metal (e.g. sodium, potassium or lithium), alkaline earth metal (e.g. magnesium or calcium) or the like; and m is an integer of 1 to 3.

Therefore, as the oxidized bromine compound represented by the general formula (2), usable in the reaction with one of the aromatic hydroxymethyl compound, aromatic alkoxymethyl compound and aromatic aldehyde compound all represented by the general formula (1), or with a mixture thereof, there can specifically be mentioned, for example, bromic acid; bromates typified by bromic acid metal salts, such as sodium bromate, potassium bromate, calcium bromate and the like which are compounds of general formula (2) wherein m is 3; bromous acid; bromites represented by bromous acid metal salts, such as sodium bromite, potassium bromite and the like which are compounds of general formula (2) wherein m is 2; hypobromous acid and hypobromites which are compounds of general formula (2) wherein m is 1. These compounds may be used as a hydrate. Use of bromic acid, bromate or bromite is preferred from the standpoints of availability, easiness of handling, reactivity, etc., and use of bromate is preferred particularly.

These oxidized bromine compounds represented by the general formula (2) are known compounds.

With respect to the molar ratio of the oxidized bromine compound represented by the general formula (2), used in the present reaction, the reaction proceeds at any molar ratio relative to the raw material compound represented by the general formula (1). However, when the raw material compound represented by the general formula (1) is either of an aromatic hydroxymethyl compound and an aromatic alkoxymethyl compound, the amount of the oxidized bromine compound represented by the general formula (2) used relative to 1 mole of the raw material compound can be, for example, ordinarily 0.66 to 1.0 mole, preferably 0.7 to 0.8 mole when the m of the general formula (2) is 3; ordinarily 1.0 to 1.5 moles, preferably 1.1 to 1.2 moles when the m of the general formula (2) is 2; and ordinarily 2.0 to 3.0 moles, preferably 2.2 to 2.4 moles when the m of the general formula (2) is 1.

When the raw material compound is an aromatic aldehyde compound, the amount of the oxidized bromine compound represented by the general formula (2) used relative to 1 mole of the raw material compound can be, for example, ordinarily 0.33 to 0.5 mole, preferably 0.35 to 0.4 mole when the m of the general formula (2) is 3; ordinarily 0.5 to 0.75 mole, preferably 0.55 to 0.6 mole when the m of the general formula (2) is 2; and ordinarily 1.0 to 1.5 moles, preferably 1.1 to 1.2 moles when the m of the general formula (2) is 1.

However, when the raw material compound represented by the general formula (1) has a plurality of groups -X (hydroxymethyl group, alkoxymethyl group or formyl group), that is, when the raw material compound is a compound of general formula (1) wherein the n is 2 to 9, or a compound of general formula (1) wherein the R is a X-substituted phenyl group or X-substituted hetero-aryl group, or a compound of general formula satisfying both of such conditions, it is necessary to use the oxidized bromine compound at a molar ratio obtained by multiplying the above-mentioned molar ratio by the total number of the substituents.

Also when the raw material compound has a plurality of groups -X, only part of the plurality of groups -X may be converted into nitrile group by controlling the molar ratio of the used oxidized bromine compound of general formula (2).

The reaction is conducted by adding ammonia or an ammonium salt as a nitrogen source. The form of ammonia added may be any; however, from the availability, aqueous ammonia or ammonia gas is preferred, and aqueous ammonia is particularly preferred.

As the ammonium salt, there can be mentioned, for example, ammonium salts of straight chain or branched chain C1 to C6 aliphatic carboxylic acids which may have substituents such as hydroxyl group, straight chain or branched chain C1 to C6 alkoxy group, straight chain or branched chain hydroxy C1 to C6 alkyl group, straight chain or branched chain (C1 to C6 alkoxy)-(C1 to C6 alkyl) group, carboxyl group or metal salt thereof, straight chain or branched chain (C1 to C6 alkoxy)carbonyl group, halogen atom, nitro group, amino group, straight chain or branched chain mono- or di(C1 to C6 alkyl)carbonylamino group, cyano group, formyl group, straight chain or branched chain (C1 to C6 alkyl)carbonyl group, phenyl group [the phenyl group may have substituents such as straight chain or branched chain C1 to C6 alkyl group, hydroxyl group, straight chain or branched chain C1 to C6 alkoxy group, straight chain or branched chain C1 to C6 hydroxyalkyl group, straight chain or branched chain (C1 to C6 alkoxy)-(C1 to C6 alkyl) group, straight chain or branched chain C1 to C6 haloalkyl group, carboxyl group or metal salt thereof, straight chain or branched chain (C1 to C6 alkoxy)carbonyl group, halogen atom, nitro group, amino group, straight chain or branched chain mono- or di(C1 to C6 alkyl)amino group, straight chain or branched chain C1 to C6 alkylcarbonylamino group, cyano group, formyl group, straight chain or branched chain (C1 to C6 alkyl)carbonyl group and the like] and the like, typified by ammonium acetate, ammonium propionate, ammonium butanoate, ammonium pentanoate, ammonium hexanoate, ammonium lactate and the like; ammonium salts of aromatic carboxylic acids which may have substituents such as straight chain or branched chain C1 to C6 alkyl group, hydroxyl group, straight chain or branched chain C1 to C6 alkoxy group, straight chain or branched chain hydroxy C1 to C6 alkyl group, straight chain or branched chain (C1 to C6 alkoxy)-(C11 to C6 alkyl) group, carboxyl group or metal salt thereof, straight chain or branched chain (C1 to C6 alkoxy)carbonyl group, halogen atom, nitro group, amino group, straight chain or branched chain mono- or di(C1 to C6) alkyl)amino group, straight chain or branched chain (C1 to C6 alkyl)carbonylamino group, cyano group, formyl group, straight chain or branched chain (C1 to C6 alkyl)carbonyl group, phenyl group [the phenyl group may have substituents such as straight chain or branched chain C1 to C6 alkyl group, hydroxyl group, straight chain or branched chain C1 to C6 alkoxy group, straight chain or branched chain C1 to C6 hydroxyalkyl group, straight chain or branched chain (C1 to C6 alkoxy)-(C1 to C6 alkyl) group, straight chain or branched chain C1 to C6 haloalkyl group, carboxyl group or metal salt thereof, straight chain or branched chain (C1 to C6 alkoxy)carbonyl group, halogen atom, nitro group, amino group, straight chain branched chain mono- or di(C1 to C6 alkyl) amino group, straight chain or branched chain C1 to C6 alkylcarbonylamino group, cyano group, formyl group, straight chain or branched chain (C1 to C6 alkyl)carbonyl group and the like] and the like, typified by ammonium benzoate, ammonium 4-chlorobenzoate, ammonium 2-methylbenzoate, ammonium 4-alkoxybenzoate, ammonium 4-hydroxybenzoate, etc.; ammonium salts of hydrogenhalide acids, typified by ammonium chloride, ammonium bromide, etc.; ammonium salts of mineral acids, typified by ammonium sulfate, ammonium phosphate, ammonium nitrate, etc.; ammonium C1 to C6 alkylsulfonates such as ammonium methanesulfonate, ammonium ethanesulfonate and the like; ammonium benzenesulfonates which may be substituted with C1 to C6 alkyl group or halogen atom, such as ammonium p-toluenesulfonate, ammonium p-benzenesulfonate, ammonium 2,4-dichlorobenzenesulfonate and the like. Preferred are ammonium carboxylates, more preferred are ammonium salts of straight chain or branched chain C1 to C6 aliphatic carboxylic acids which may have substituents, particularly preferred are ammonium acetate and ammonium propionate.

The amount of ammonia or ammonium salt used is at least an equivalent relative to the raw material compound used and may be ordinarily 1.0 to 5.0 equivalents and preferably 1.0 to 3.0 equivalents relative to 1 mole of the raw material compound represented by the general formula (1).

However, when the raw material compound represented by the general formula (1) has a plurality of groups -X (hydroxymethyl group, alkoxymethyl group or formyl group), that is, when the raw material compound is a compound of general formula (1) wherein the n is 2 to 9, or a compound of general formula (1) wherein the R is a X-substituted phenyl group or X-substituted hetero-aryl group, or a compound of general formula (1) satisfying both of such conditions, it is preferred to use the ammonia or ammonium salt at equivalents obtained by multiplying the above-mentioned equivalents of ammonia or ammonium salt by the total number of the substituents.

Use of an amine (primary amine, secondary amine or tertiary amine) in place of the ammonia or ammonium salt is not desired because it produces an amide compound (a by-product) besides an intended product) or because an intended reaction does not proceed smoothly and no intended product is obtained at all.

The reaction is conducted using an acid catalyst. As the acid catalyst used in the reaction, there can be mentioned, for example, carboxylic acids such as acetic acid, propionic acid, trifluoroacetic acid, fluoroacetic acid, lactic acid, amino acids and the like; organic acids typified by organic sulfonic acids such as p-toluenesulfonic acid, methanesulfonic acid, benzenesulfonic acid and the like; inorganic acids such as hydrochloric acid, sulfuric acid, phosphoric acid and the like; Lewis acids such as aluminum chloride, boron trifluoride-tetrahydrofuran complex ($BF_3$-THF complex), polyphosphoric acid and the like; and solid acids. Use of carboxylic acid such as acetic acid, propionic acid or the like is preferred in the reaction.

The amount of the acid catalyst used in the reaction may be any amount as long as the reaction proceeds sufficiently. However, the amount is, for example, 0.01 to 100 moles, preferably 0.05 to 30 moles, more preferably 0.1 to 30 moles, particularly preferably 0.2 to 10 moles per 1 mole of the raw material compound represented by the general formula (1). In the reaction, the above molar ratio is sufficient when the raw material compound is neutral.

Meanwhile, for example, when the hetero-cycle portion of the raw material compound shows basicity and is in a neutral state (that is, does not take a form of salt such as hydrochloride or the like), it is presumed that the acid catalyst forms a substance like an ion pair, with the raw material compound in the reaction system and accordingly the amount of the acid catalyst required to exhibit an intended function decreases in the reaction system; therefore, it is preferred that, for example, the acid catalyst is used excessively by an amount matching the number of basic portion in the hetero-cyclic aromatic compound molecule represented by the general formula (1) and the amount of the acid catalyst capable of exhibiting its intended function is controlled in the above-mentioned range of the use amount of the acid catalyst. The use amount of the acid catalyst may not be limited to the above-mentioned range and may be a large excess when later.

The reaction may take place sufficiently in a solvent-free state but may also be conducted using a solvent. The solvent usable in the reaction may be any solvent as long as it does not hinder the reaction. There can be mentioned, for example, carboxylic acids such as acetic acid, propionic acid and the like; water; aromatic hydrocarbons such as toluene, xylene, chlorobenzene and the like; halogenated aliphatic hydrocarbons such as dichloromethane, chloroform and the like; acetic acid esters such as methyl acetate, ethyl acetate, butyl acetate and the like; aprotic polar solvents such as dimethylformamide, dimethylacetamide, N-methylpyrrolidone, tetramethylurea, hexamethylphosphoric triamide (HMPA), propylene carbonate and the like; ether type solvents such as diethyl ether, tetrahydrofuran, dioxane and the like; and aliphatic hydrocarbons such as pentane, n-hexane and the like. Use of carboxylic acid (e.g. acetic acid, propionic acid) or water is preferred from the standpoints of solubility and reactivity of oxidizing reagent (oxidized bromine compound), and use of carboxylic acid as the solvent is particularly preferred because the carboxylic acid functions also as an acid catalyst. The solvent may be used singly or as a mixed solvent of any mixing ratio.

The amount of the solvent used may be an amount enabling sufficient stirring of the reaction system. However, the amount is ordinarily 0.05 to 10 liters, preferably 0.5 to 2 liters relative to 1 mole of the raw material compound represented by the general formula (1). Use of a solvent of too low polarity is not desired because it reduces the solubility of oxidizing reagent (oxidized bromine compound), which may retard the reaction.

The reaction may be conducted by feeding, at one time, materials necessary in the reaction, such as raw material compound represented by the general formula (1), catalyst, an oxidized bromine compound represented by the general formula (2), ammonia or ammonium salt, solvent and the like. However, from the standpoint of easier removal of the heat generated in the reaction, it is preferred to use, for example, a process which comprises feeding the oxidized bromine compound represented by the general formula (2), in a solid form per se in portions, a process which comprises making the oxidized bromine compound represented by the general formula (2) into a slurry using a solvent (e.g. water) and then adding the slurry gradually, or a process which comprises adding dropwise an aqueous solution or hot aqueous solution of the oxidized bromine compound represented by the general formula (2); and it is particularly preferred to use a process which comprises adding dropwise an aqueous solution or hot aqueous solution of the oxidized bromine compound represented by the general formula (2).

The temperature of the reaction is 50° C. to the reflux temperature of the solvent used, preferably 70° C. to the reflux temperature of the solvent used, particularly preferably 70° C. to 100° C.

Incidentally, when the reaction is conducted at high temperatures, heat may be generated vigorously with the vigorous proceeding of the reaction, depending upon the scale of the reaction. Therefore, it is advantageous in some cases to, for example, carefully set the reaction temperature low or dropwise add the present raw material compound into the reaction system.

The time of the reaction is not restricted particularly. However, it is preferred to be 1 to 30 hours from the standpoint of, for example, suppression of by-product formation.

According to the present reaction, an aromatic nitrile compound represented by the general formula (3) is formed at a high selectivity under mild conditions without using any special reactor or an excessive amount of an oxidizing reagent (oxidized bromine compound) or a nitrogen source. The obtained aromatic nitrile compound represented by the general formula (3) is a compound which is useful as an intermediate for medicine, agricultural chemical, etc.

Next, the process for producing the present invention compound is described specifically by way of Examples. However, the present invention is in no way restricted by these Examples.

EXAMPLE 1

Production of 2-cyano-5-methylthiophene

Into a 50 ml, three-necked flask equipped with a magnetic stirrer, a reflux condenser and a thermometer were added 6.3 g (50 mmol) of 2-formyl-5-methylthiophene, 3.0 g (20 mmol) of sodium bromate, 10 ml (174 mmol) of acetic acid and 5 g (74 mmol) of 25% aqueous ammonia, followed by stirring at 80° C. for 4 hours. To the reaction mixture were added 30 ml of water and 50 ml of ether. Further, an aqueous solution containing 23% of sodium hydroxide was added carefully until a pH of >11 was reached. The mixture was subjected to phase separation. Then, there were conducted washing with water and a saturated aqueous sodium chloride solution in this order, drying over anhydrous sodium sulfate, and distillation under reduced pressure for ether removal, to obtain 6.5 g of an oil as a residue. The oil was subjected to Kugel-rohr distillation to obtain 5.9 g of a colorless oil. The oil contained, as a component, 94.0% (in terms of areal ratio of liquid chromatography) (yield: 96.0%) of 2-cyano-5-methylthiophene. Liquid mass chromatography was conducted to confirm a molecular ion peak $[(M-1)^+]$ of 122.

EXAMPLE 2

Production of 2-furonitrile

Into a 15 ml, test tube-shaped reactor equipped with a magnetic stirrer and a reflux condenser were added 0.38 g (4 mmol) of furfural, 0.2 g (1.35 mmol) of sodium bromate, 2 ml (34.8 mmol) of acetic acid and 0.3 g (4.4 mmol) of 25% aqueous ammonia, followed by stirring at 70° C. for 3 hours. The reaction mixture contained, as components, 34.8% (in terms of areal ratio of gas chromatography) of 2-furonitrile and 65.2% of furfural. Gas mass chromatography was conducted to confirm a molecular ion peak $[M^+]$ of 93.

EXAMPLE 3

Production of 2-furonitrile

Into a 15 ml, test tube-shaped reactor equipped with a magnetic stirrer and a reflux condenser were added 0.38 g (4 mmol) of furfural, 0.2 g (1.35 mmol) of sodium bromate, 0.4 g (6.7 mmol) of acetic acid, 0.35 g (5 mmol) of 25% aqueous ammonia and 1 ml of water, followed by stirring at 90° C. for 2 hours. The reaction mixture contained, as components, 61.5% (in terms of areal ratio of gas chromatography) of 2-furonitrile and 38.5% of furfural. Gas mass chromatography was conducted to confirm a molecular ion peak $[M^+]$ of 93.

EXAMPLE 4

Production of 4-quinolinecarbonitrile

Into a 15 ml, test tube-shaped reactor equipped with a magnetic stirrer and a reflux condenser were added 0.71 g (4.5 mmol) of 4-quinolinecarboaldehyde, 0.27 g (1.8 mmol) of sodium bromate, 0.6 g (10 mmol) of acetic acid, 0.35 g (5 mmol) of 25% aqueous ammonia and 1 ml of water, followed by stirring at 90° C. for 2 hours. The reaction mixture contained, as a component, 97.4% (in terms of areal ratio of gas chromatography) of 4-quinolinecarbonitrile. To the reaction mixture were added 30 ml of a saturated aqueous sodium bicarbonate solution and 30 ml of ethyl acetate. The mixture was subjected to phase separation. Then, there were conducted washing with a saturated aqueous sodium chloride solution, drying over anhydrous sodium sulfate, and distillation under reduced pressure for ethyl acetate removal. The residue was purified by silica gel column chromatography (ethyl acetate/n-hexane=1:1 v/v) to obtain 0.35 g (yield: 50.5%) of white crystals. Gas mass chromatography was conducted to confirm a molecular ion peak $[M^+]$ of 154.

EXAMPLE 5

Production of 3-cyanopyridine

Into a 50 ml, eggplant-shaped flask equipped with a magnetic stirrer and a reflux condenser were added 2.18 g (20 mmol) of 3-pyridylmethanol, 2.25 g (15 mmol) of sodium bromate, 3.0 g (50 mmol) of acetic acid, 1.5 g (22 mmol of 25% aqueous ammonia and 5 ml of water, followed by stirring at 95° C. for 2 hours. The reaction mixture contained, as a component, 95.2% (in terms of areal ratio of gas chromatography) of 3-cyanopyridine. To the reaction mixture were added 50 ml of a saturated aqueous sodium bicarbonate solution and 50 ml of ethyl acetate. The mixture was subjected to phase separation. The aqueous phase was subjected to extraction using 50 ml of ethyl acetate. The ethyl acetate phase was combined. The mixture was washed with a saturated aqueous sodium chloride solution, dried over anhydrous sodium sulfate, and subjected to distillation under reduced pressure for ethyl acetate removal. The resi-

EXAMPLE 6

Production of 2-cyanothiazole

Into a 15 ml, test tube-shaped reactor equipped with a magnetic stirrer and a reflux condenser were added 0.22 g (2 mmol) of 2-formylthiazole, 0.12 g (0.8 mmol) of sodium bromate, 1.0 g (16.7 mmol) of acetic acid, 0.25 g (3.6 mmol) of 25% aqueous ammonia and 1 ml of water, followed by stirring at 90° C. for 2 hours. The reaction mixture contained, as a component, 67.6% (in terms of areal ratio of gas chromatography) of 2-cyanothiazole. Gas mass chromatography was conducted to confirm a molecular ion peak [M$^+$] of 110.

REFERENCE EXAMPLE 1

Synthesis of 2-formyl-5-methylthiophene

Into a 50 ml, three-necked flask equipped with a magnetic stirrer, a reflux condenser and a thermometer were added 10.9 g (0.15 mol) of dimethylformamide and 15.3 g (0.15 mol) of phosphorus oxychloride. The mixture was cooled to 0° C. with stirring. Then, 9.8 g (0.1 mol) of 2-methylthiophene was added to the system, followed by stirring at 25 to 35° C. for 18 hours. To the reaction mixture were added 30 ml of water and 50 ml of ether. Further, an aqueous solution containing 23% of sodium hydroxide was added carefully until a pH of >11 was reached. The mixture was subjected to phase separation. Then, there were conducted washing with a saturated aqueous sodium chloride solution, drying pressure for ether removal. The residue was subjected to Kugel-rohr distillation to obtain 10.1 g of a colorless oil. The oil contained, as a component, >99.9% (in terms of areal ratio of gas chromatography) (yield: 80.2%) of 2-formyl-5-methylthiophene. Gas mass chromatography was conducted to confirm a molecular ion peak [M$^+$] of 126.

EXAMPLE 7

Production of p-chlorobenzonitrile

Into a 50 ml, three-necked flask equipped with a magnetic stirrer, a reflux condenser and a thermometer were added 5.62 g (40 mmol) of p-chlorobenzaldehyde, 2.2 g (14.85 mmol) of sodium bromate, 10 ml (174 mmol) of acetic acid and 3 g (44 mmol) of 25% aqueous ammonia, followed by stirring at 105° C. for 4 hours. With progress of a reaction, a small amount of bromine was formed. To the reaction mixture were added 30 ml of water and 50 ml of ethyl acetate. Further, an aqueous solution containing 23% of sodium hydroxide was added until a pH of >11 was reached. The mixture was subjected to phase separation. The aqueous phase was subjected to extraction using 30 ml of ethyl acetate. The ethyl acetate phase was combined and the resulting mixture was washed with water and a saturated aqueous sodium chloride solution in this order, dried over anhydrous sodium sulfate, and subjected to distillation under reduced pressure for ethyl acetate removal, to obtain 5.3 g of white crystals of p-chlorobenzonitrile. The crystals contained, as a component, >99.9% (in terms of areal ratio of gas chromatography) (yield: 96.3%) of p-chlorobenzonitrile. Gas mass chromatography (GC-MS) was conducted and the molecular ion peak [M$^+$] of p-chlorobenzonitrile was confirmed to be 137.

EXAMPLE 8

Production of benzonitrile

Into a 15 ml, test tube-shaped reactor equipped with a magnetic stirrer and a reflux condenser were added 0.43 g (4 mmol) of benzyl alcohol, 0.4 g (2.7 mmol) of sodium bromate, 2 ml (34.8 mmol) of acetic acid and 0.4 g (5.9 mmol) of 25% aqueous ammonia, followed by stirring at 90° C. for 15 hours. The reaction mixture contained, as a component, >99.9% (in terms of areal ratio of gas chromatography) of benzonitrile. Gas mass chromatography (GC-MS) was conducted and the molecular ion peak [M$^+$] of benzonitrile was confirmed to be 103.

EXAMPLE 9

Production of benzonitrile

An operation was conducted in the same manner as in Example 8 except that benzyl alcohol was replaced by 0.42 g (4 mmol) of benzaldehyde and sodium bromate was used by 0.2 g (1.35 mmol). The reaction mixture contained, as a component, >99.9% (in terms of areal ratio of gas chromatography) of benzonitrile. Gas mass chromatography (GC-MS) was conducted and the molecular ion peak [M$^+$] of benzonitrile was confirmed to be 103.

EXAMPLE 10

Production of p-nitrobenzonitrile

An operation was conducted in the same manner as in Example 9 except that benzaldehyde was replaced by 0.6 g (4 mmol) of p-nitrobenzaldehyde and 25% aqueous ammonia was used by 0.31 g (4.6 mmol). The reaction mixture contained, as a component, >99.9% (in terms of areal ratio of gas chromatography) of p-nitrobenzonitrile. Gas mass chromatography (GC-MS) was conducted and the molecular ion peak [M$^+$] of p-nitrobenzonitrile was confirmed to be 148.

EXAMPLE 11

Production of o-fluorobenzonitrile

An operation was conducted in the same manner as in Example 10 except that p-nitrobenzaldehyde was replaced by 0.42 g (4 mmol) of o-fluorobenzaldehyde. The reaction mixture contained, as a component, >99.9% (in terms of areal ratio of gas chromatography) of o-fluorobenzonitrile. Gas mass chromatography (GC-MS) was conducted and the molecular ion peak [M$^+$] of o-fluorobenzonitrile was confirmed to be 121.

EXAMPLE 12

Production of p-methylbenzonitrile

An operation was conducted in the same manner as in Example 10 except that p-nitrobenzaldehyde was replaced by 0.42 g (4 mmol) of p-methylbenzaldehyde. The reaction mixture contained, as components, 97.8% (in terms of areal ratio of gas chromatography) of p-methylbenzonitrile and 2.2% of p-methylbenzaldehyde. Gas mass chromatography (GC-MS) was conducted and the molecular ion peak [M+] of p-methylbenzonitrile was confirmed to be 117.

EXAMPLE 13

Production of p-chlorobenzonitrile

An operation was conducted in the same manner as in Example 8 except that p-nitrobenzaldehyde was replaced by 0.31 g (2 mmol) of p-chlorobenzyl methyl ether and 25% aqueous ammonia was used by 0.31 g (4.6 mmol). The reaction mixture contained, as components, 94.0% (in terms of areal ratio of gas chromatography) of p-chlorobenzonitrile, 2.3% of p-chlorobenzyl methyl ether and 3.7% of methyl p-chlorobenzoate. Gas mass chromatography (GC-MS) was conducted and the molecular ion peak [M+] of p-chlorobenzonitrile was confirmed to be 137.

EXAMPLE 14

Production of benzonitrile

An operation was conducted in the same manner as in Example 9 except that sodium bromate was replaced by 0.27 g (2 mmol) of sodium bromite. The reaction mixture contained, as components, 79.0% (in terms of areal ratio of gas chromatography) of benzonitrile and 17.3% of benzaldehyde. Gas mass chromatography (GC-MS) was conducted and the molecular ion peak [M+] of benzonitrile was confirmed to be 103.

EXAMPLE 15

Production of benzonitrile

An operation was conducted in the same manner as in Example 9 except that sodium bromate was replaced by 0.23 g (1.35 mmol) of potassium bromate. The reaction mixture contained, as components, 88.2% (in terms of areal ratio of gas chromatography) of benzonitrile and 7.4% of benzaldehyde. Gas mass chromatography (GC-MS) was conducted and the molecular ion peak [M+] of benzonitrile was confirmed to be 103.

EXAMPLE 16

Production of benzonitrile

An operation was conducted in the same manner as in Example 9 except that acetic acid was replaced by 2 ml (26.8 mmol) of propionic acid. The reaction mixture contained, as components, 92.1% (in terms of areal ratio of gas chromatography) of benzonitrile and 6.4% of benzaldehyde. Gas mass chromatography (GC-MS) was conducted and the molecular ion peak [M+] of benzonitrile was confirmed to be 103.

EXAMPLE 17

Production of benzonitrile

An operation was conducted in the same manner as in Example 9 except that acetic acid was replaced by 2 ml (21.9 mmol) of n-butanoic acid. The reaction mixture contained, as components, 92.8% (in terms of areal ratio of gas chromatography) of benzonitrile and 7.2% of benzaldehyde. Gas mass chromatography (GC-MS) was conducted and the molecular ion peak [M+] of benzonitrile was confirmed to be 103.

EXAMPLE 18

Production of p-cyanobenzonitrile

An operation was conducted in the same manner as in Example 10 except that benzaldehyde was replaced by 0.28 g (2 mmol) of p-xylylene glycol and sodium bromate was used by 0.4 g (2.7 mmol). The reaction mixture contained, as a component, 93.5% (in terms of areal ratio of gas chromatography) of p-cyanobenzonitrile. Gas mass chromatography (GC-MS) was conducted and the molecular ion peak [M+] of p-cyanobenzonitrile was confirmed to be 128.

EXAMPLE 19

Production of benzonitrile Using a Mixture of Raw Material Compounds

Into a 15 ml, test tube-shaped reactor equipped with a magnetic stirrer and a reflux condenser were added 0.22 g (2 mmol) of benzyl alcohol, 0.21 g (2 mmol) of benzaldehyde, 0.30 g (2 mmol) of sodium bromate, 2 ml (34.8 mmol) of acetic acid and 0.4 g (5.9 mmol) of 25% aqueous ammonia, followed by stirring at 90° C. for 3 hours. The reaction mixture contained, as a product, 94.6% (in terms of areal ratio of gas chromatography) of benzonitrile, and benzaldehyde remained by 4.4%. Gas mass chromatography (GC-MS) was conducted and the molecular ion peak [M+] of benzonitrile was confirmed to be 103.

EXAMPLE 20

Production of p-chlorobenzonitrile using a Mixture of Raw Material Compounds

Into a 15 ml, test tube-shaped reactor equipped with a magnetic stirrer and a reflux condenser were added 0.31 g (2 mmol) of p-chlorobenzyl methyl ether, 0.31 g (2.2 mmol) of p-chlorobenzaldehyde, 0.33 g (2.2 mmol) of sodium bromate, 2 ml (34.8 mmol) of acetic acid and 0.4 g (5.9 mmol) of 25% aqueous ammonia, followed by stirring at 90° C. for 4 hours. The reaction mixture contained, as a product, 94.7% (in terms of areal ratio of gas chromatography) of p-chlorobenzonitrle, and p-chlorobenzyl methyl ether remained by 4.1%. Gas mass chromatography (GC-MS) was conducted and the molecular ion peak [M+] of p-chlorobenzonitrile was confirmed to be 137.

COMPARATIVE EXAMPLE 1

Production of benzonitrile in Absence of Acid Catalyst

An operation was conducted in the same manner as in Example 8 except that 2 ml of acetic acid was replaced by 2 ml of propylene carbonate and there were used 0.2 g (1.35 mmol) of sodium bromate and 0.31 g (4.6 mmol) of 25% aqueous ammonia. In the reaction mixture, 98.7% (in terms of areal ratio of gas chromatography) of benzaldehyde used as a raw material remained, and formation of intended benzonitrile did not proceed substantially.

COMPARATIVE EXAMPLE 2

Production of benzonitrile Using Sodium Chlorate

An operation was conducted in the same manner as in Example 8 except that sodium bromate was replaced by 0.14 g (1.35 mmol) of sodium chlorate and there was used 0.31 g (4.6 mmol) of 25% aqueous ammonia. In the reaction mixture, 100% (in terms of areal ratio of gas chromatography) of benzaldehyde used as a raw material remained, and there was no formation of intended benzonitrile.

COMPARATIVE EXAMPLE 3

Production of benzonitrile Using Methyl Amine

An operation was conducted in the same manner as in Example 8 except that 25% aqueous ammonia was replaced by 0.35 g (4.5 mmol) of 40% methylamine. The reaction mixture contained, as components, 12.4% (in terms of areal ratio of gas chromatography) of intended benzonitrile, 32.1% of N-methylbenzamide (a by-product) and 45.7% of benzaldehyde used as a raw material.

INDUSTRIAL APPLICABILITY

As described above, the present invention provides a novel process for industrially producing an aromatic nitrile compound. In the present invention process, there can be freely selected, as a raw material, one of an aromatic hydroxymethyl compound, an aromatic alkoxymethyl compound and an aromatic aldehyde compound, all represented by the general formula (1), which are all highly available, or a mixture thereof; an intended aromatic nitrile compound can be produced at a high selectivity under mild conditions and in an easy operation without using any special reactor or any expensive catalyst or any transition metal; no harmful waste derived from catalyst or transition metal used is generated, which makes waste disposal easy and friendly to the environment; thus, the present process has high industrial applicability.

The invention claimed is:

1. A process for producing an aromatic nitrile compound represented by the following general formula (3):

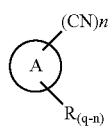

(3)

[wherein ring A is an aromatic hetero-cycle having at least one hetero-atom or a phenyl ring;

n is an integer of 1 to 9;

R is a hydrogen atom, an alkyl group, a hydroxyl group, an alkoxy group, a hydroxyalkyl group, an alkoxyalkyl group, a haloalkyl group, a carboxyl group or a metal salt thereof, an alkoxycarbonyl group, a halogen atom, a nitro group, an amino group, an alkylamino group, a dialkylamino group, an alkylcarbonylamino group, a cyano group, a formyl group, an alkylcarbonyl group, or a substituted or unsubstituted phenyl group; q is an integer of 1 to 9 with a proviso that (q−n) is zero or a positive integer; when (q−n) is 2 or more, a plurality of Rs may be the same or different; two Rs may be bonded to each other to form a ring], characterized in that one of an aromatic hydroxymethyl compound, an aromatic alkoxymethyl compound and an aromatic aldehyde compound, all represented by the following general formula (1):

(1)

(wherein X is a hydroxymethyl group, an alkoxymethyl group or a formyl group; n, R and q have the same definitions as given above), or a mixture thereof is reacted with an oxidized bromine compound represented by the general formula (2)

$$MBrO_m \qquad (2)$$

(wherein M is a hydrogen atom or a metal atom, and m is an integer of 1 to 3) in the presence of an acid catalyst and either ammonia or an ammonium salt.

2. A process for producing an aromatic nitrile compound according to claim 1, wherein the ring A is an aromatic hetero-cycle having at least one hetero-atom.

3. A process for producing an aromatic nitrile compound according to claim 2, wherein the hetero-atom is selected from the group consisting of nitrogen atom, oxygen atom and sulfur atom.

4. A process for producing an aromatic nitrile compound according to claim 2, wherein the ring A is a 5- to 10-membered aromatic hetero-ring having 1 to 3 hetero-atoms selected from the group consisting of nitrogen atom, oxygen atom and sulfur atom.

5. A process for producing an aromatic nitrile compound according to claim 2, wherein the ring A is a furan ring, a thiophene ring, a pyridine ring, a quinoline ring or a thiazole ring.

6. A process for producing an aromatic nitrile compound according to claim 1, wherein the ring A is a phenyl ring.

7. A process for producing an aromatic nitrile compound according to claim 1, wherein the raw material compound represented by the general formula (1) is a compound of the general formula (1) wherein all of a plurality of Rs are hydrogen atom or at least one of a plurality of Rs is an electron-attractive group or an alkyl group.

8. A process for producing an aromatic nitrile compound according to claim 7, wherein the compound represented by the general formula (1) is a compound of the general formula (1) wherein all of a plurality of Rs are hydrogen atom or at least one of a plurality of Rs is a chloro group, a nitro group, a fluoro group or a methyl group.

* * * * *